United States Patent
Tearney et al.

(10) Patent No.: US 12,032,181 B2
(45) Date of Patent: Jul. 9, 2024

(54) SYSTEM AND METHOD FOR HIGH-RESOLUTION, HIGH-SPEED CAPSULE ENDOMICROSCOPY

(71) Applicant: The General Hospital Corporation, Boston, MA (US)

(72) Inventors: Guillermo J. Tearney, Cambridge, MA (US); Jiheun Ryu, Cambridge, MA (US)

(73) Assignee: The General Hospital Corporation, Boston, MA (US)

( * ) Notice: Subject to any disclaimer, the term of this patent is extended or adjusted under 35 U.S.C. 154(b) by 621 days.

(21) Appl. No.: 17/002,572

(22) Filed: Aug. 25, 2020

(65) Prior Publication Data

US 2021/0063618 A1     Mar. 4, 2021

Related U.S. Application Data

(60) Provisional application No. 62/892,073, filed on Aug. 27, 2019.

(51) Int. Cl.
*G02B 5/18* (2006.01)
*A61B 1/00* (2006.01)
(Continued)

(52) U.S. Cl.
CPC ........ *G02B 5/1814* (2013.01); *A61B 1/00165* (2013.01); *A61B 1/00188* (2013.01);
(Continued)

(58) Field of Classification Search
CPC .............. G02B 5/1814; G02B 21/0028; G02B 23/2469; G02B 23/243; G02B 3/04;
(Continued)

(56) References Cited

U.S. PATENT DOCUMENTS 6,831,781 B2   12/2004   Tearney
7,334,459 B2   2/2008    Chen
(Continued)

FOREIGN PATENT DOCUMENTS

EP   1329189 B1      1/2004
WO   2010090837 A2   8/2010
(Continued)

OTHER PUBLICATIONS

Oh et al.,">400 kHz repetition rate wavelength-swept laser and application to high-speed optical frequency domain imaging" Optical Letters, vol. 35, No. 17, pp. 2919-2921, 2010. (Year: 2010).*
(Continued)

*Primary Examiner* — George G. King
*Assistant Examiner* — Anna Elizabeth Smith
(74) *Attorney, Agent, or Firm* — Quarles & Brady LLP

(57) ABSTRACT

A probe for performing endomicroscopy, including: a light source; a waveguide coupled to the light source; a diffraction grating, the waveguide directing light from the light source to the diffraction grating; and a lens having a first aspheric surface and a second biconic surface, diffracted light from the diffraction grating being directed into the aspheric surface of the lens and being emitted from the biconic surface of the lens towards a transparent cylindrical surface of the probe.

34 Claims, 9 Drawing Sheets

(51) Int. Cl.
  *A61B 1/04* (2006.01)
  *A61B 5/00* (2006.01)
  *G02B 21/00* (2006.01)
  *G02B 23/24* (2006.01)

(52) U.S. Cl.
  CPC ............ *A61B 1/041* (2013.01); *A61B 5/0068* (2013.01); *G02B 21/0028* (2013.01); *G02B 23/2469* (2013.01); *A61B 1/00096* (2013.01); *G02B 23/243* (2013.01)

(58) Field of Classification Search
  CPC ... G02B 3/06; A61B 1/00165; A61B 1/00188; A61B 1/041; A61B 1/00096; A61B 5/0068
  See application file for complete search history.

(56) References Cited

U.S. PATENT DOCUMENTS

| | | | |
|---|---|---|---|
| 7,843,572 B2 | 11/2010 | Tearney et al. | |
| 9,295,391 B1 | 3/2016 | Tearney | |
| 9,671,606 B2 * | 6/2017 | Fujii | ............ A61B 1/07 |
| 9,733,460 B2 | 8/2017 | Kang | |
| 9,841,571 B1 | 12/2017 | Momtahan | |
| 2002/0186478 A1 * | 12/2002 | Watanabe | ............ G02B 23/243 359/811 |
| 2009/0147373 A1 * | 6/2009 | Rolland | ............ A61B 5/0084 359/665 |
| 2009/0153974 A1 * | 6/2009 | Sales | ............ G02B 3/0043 359/599 |
| 2011/0137178 A1 | 6/2011 | Tearney | |
| 2013/0310643 A1 * | 11/2013 | Gora | ............ A61B 5/0062 600/109 |
| 2014/0221753 A1 | 8/2014 | Tearney | |
| 2015/0049339 A1 | 2/2015 | Tearney | |
| 2016/0299170 A1 * | 10/2016 | Ito | ............ G02B 23/26 |
| 2017/0307872 A1 * | 10/2017 | Hatase | ............ H04N 23/51 |
| 2020/0085285 A1 * | 3/2020 | Yamada | ............ A61B 1/00057 |

FOREIGN PATENT DOCUMENTS

| | | |
|---|---|---|
| WO | 2014157645 A1 | 10/2014 |
| WO | 2020159844 A1 | 8/2020 |

OTHER PUBLICATIONS

Axsun. Swept Lasers for OCT. Product Sheet. Version accessed on Nov. 30, 2020. https://web.archive.org/web/20201130210557/https://downloads.axsun.com/public/datasheets/Axsun_OCT_laser_datasheet.pdf. Two pages.

Grulkowski, I., et al. "Retinal, anterior segment and full eye imaging using ultrahigh speed swept source OCT with vertical-cavity surface emitting lasers." Biomedical optics express 3.11 (2012): 2733-2751.

International Searching Authority. International Search Report and Written Opinion for application PCT/US2020/047826, dated Nov. 17, 2020. Ten pages.

Kang, D., et al. "A miniaturized, tethered, spectrally-encoded confocal endomicroscopy capsule." Lasers in surgery and medicine 51.5 (2019): 452-458.

Kang, D., et al. "Endoscopic probe optics for spectrally encoded confocal microscopy." Biomedical Optics Express 4.10 (2013): 1925.

Tabatabaei, N., et al. "Clinical translation of tethered confocal microscopy capsule for unsedated diagnosis of eosinophilic esophagitis." Scientific reports 8.1 (2018): 1-9.

Thorlabs Inc. Apsheric Lens f=4.51 mm NA = 0.55 [online] Feb. 21, 2007. Retrieved from https://www.thorlabs.com/drawings/cc84dd06dd2829dd-A1A49955-E725-34EE-2C1A33DB20BF7CB1/350230-B-AutoCADPDF.pdf.

Japan Patent Office, Notification of Reasons for Refusal, Application No. 2022-513083, dated Mar. 14, 2023, 12 pages.

Japan Patent Office, Notification of Reasons for Refusal, Application No. 2022-513083, dated Jul. 11, 2023, 15 pages.

Bernet, Zoomable Telescope by Rotation of Toroidal Lenses, arXiv:1807.07733v1, Jul. 20, 2018, 9 pages.

European Patent Office, Extended Search Report, Application No. 20858707.1, Aug. 17, 2023, 10 pages.

\* cited by examiner

| | SEGMENT 910 | SEGMENT 1060 |
|---|---|---|
| Immersion medium | Water | None |
| Central wavelength | 1290nm | 1060nm |
| Capsule diameter | 7mm | 8mm |
| Imaging field-of-view | 260μm | 340μm |
| Lateral resolution | 1.44μm | 1.25um |
| Target imaging depth | 50μm | 100μm |
| Imaging angle | 95.725° | 90° |

FIG. 9

SYSTEM AND METHOD FOR HIGH-RESOLUTION, HIGH-SPEED CAPSULE ENDOMICROSCOPY

CROSS-REFERENCE TO RELATED APPLICATIONS

This application is based on, claims the benefit of, and claims priority to U.S. Provisional Application No. 62/892,073, filed Aug. 27, 2019, which is hereby incorporated herein by reference in its entirety for all purposes.

STATEMENT REGARDING FEDERALLY SPONSORED RESEARCH

N/A

BACKGROUND

Spectrally encoded confocal microscopy (SECM) is a high-speed imaging technique that can provide 1-2 orders of magnitude faster imaging speed compared to video rate reflectance confocal microscopy, while enabling a high degree of probe miniaturization by replacing a mechanical scanning device with a diffraction grating. However, in prior designs asymmetric spherical aberrations caused at a probe surface (for example, arising from the cylindrical imaging window of an SECM capsule) have made it difficult to achieve diffraction-limited optical resolution. One solution to this has been to fill the gap between the objective lens and the imaging window in the probe (e.g. capsule) with water to minimize aberrations by reducing the refractive index mismatch in an effort to provide diffraction-limited optical resolution (see FIG. 1, panels A and B). Panel A of FIG. 1 shows an objective lens of a known system which has rounded surfaces on both sides, where both of the rounded surfaces are radially symmetric.

However, filling a probe such as an SECM capsule with water poses a number of additional manufacturing requirements including a need to seal components with water-tight epoxy. In addition, the lifetime of water-filled SECM capsules is reduced (e.g. less than 1-2 months) due to the difficulty of keeping water inside the probe. Finally, air bubbles within the water may appear inside the probe during procedures, which can interfere with optimal performance (see FIG. 2).

SUMMARY OF THE PRESENT DISCLOSURE

Thus, a new SECM probe design was sought which does not require filling the probe with a liquid such as water but which nevertheless provides comparable optical performance.

Accordingly, presented herein are embodiments of a probe for performing endomicroscopy, including: a light source; a waveguide coupled to the light source; a diffraction grating, the waveguide directing light from the light source to the diffraction grating; and a lens having a first aspheric surface and a second biconic surface, diffracted light from the diffraction grating being directed into the aspheric surface of the lens and being emitted from the biconic surface of the lens towards a transparent cylindrical surface of the probe.

In one embodiment, the invention provides a method for performing endomicroscopy using a probe. The probe includes: a light source, a waveguide coupled to the light source, a diffraction grating, and a lens having a first aspheric surface and a second biconic surface. The method includes the waveguide directing light from the light source to the diffraction grating, and the diffraction grating directing diffracted light into the aspheric surface of the lens and being emitted from the biconic surface of the lens towards a transparent cylindrical surface of the probe.

These and other embodiments, aspects, advantages, and features of the present invention will be set forth in part in the description which follows, and will become apparent to those skilled in the art by reference to the following description of the invention and referenced drawings or by practice of the invention. The accompanying drawings illustrate one or more implementations, and these implementations do not necessarily represent the full scope of the invention.

BRIEF DESCRIPTION OF THE DRAWINGS

FIG. 9 shows a table comparing specifications of an existing SECM-based, water-immersion capsule to an SECM capsule that includes an objective lens having a biconic surface and which does not require water immersion.

Figure 1:
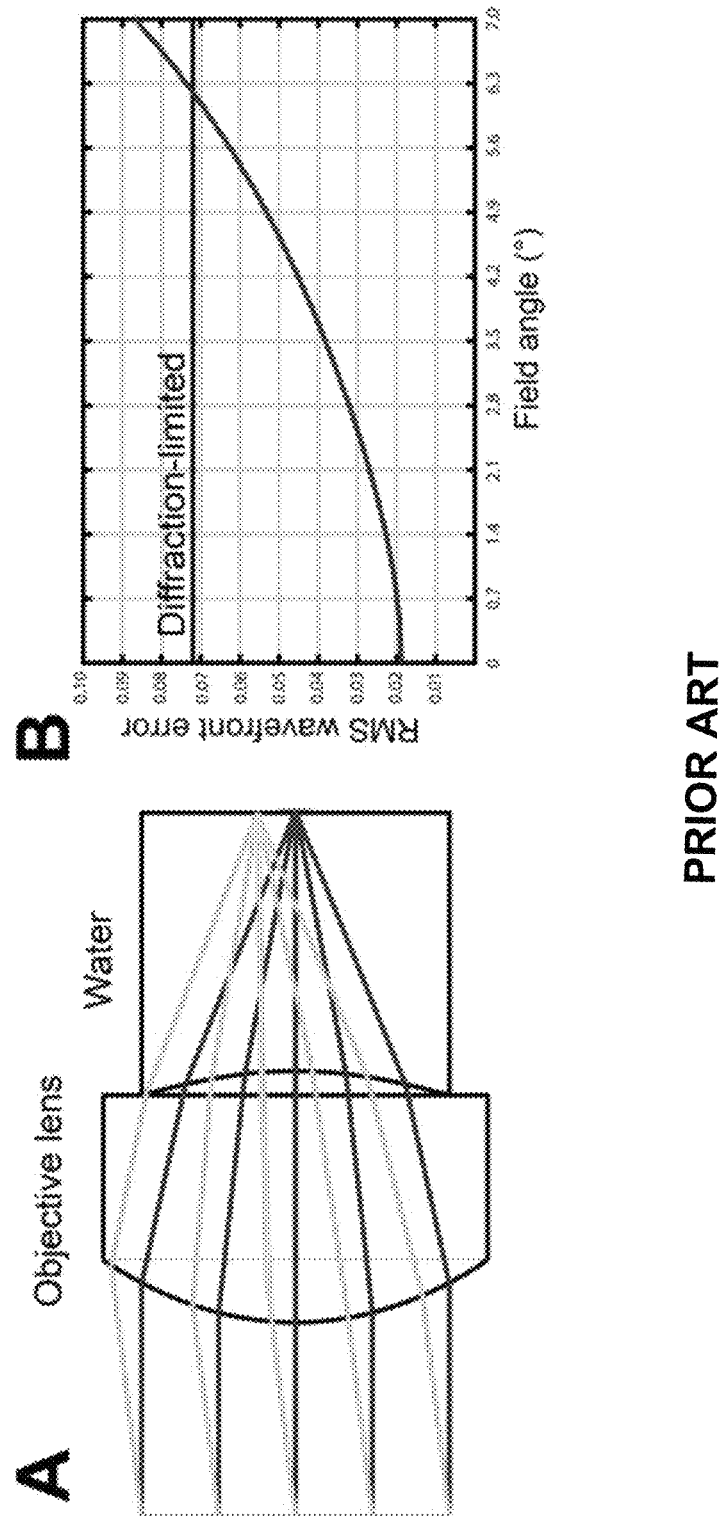
FIG. 1 shows a ZEMAX simulation of an SECM objective lens which does not have a biconic surface; panel A shows a layout of the objective lens with ray tracing, and panel B shows RMS wavefront error as a function of the field angle.
Figure 2:
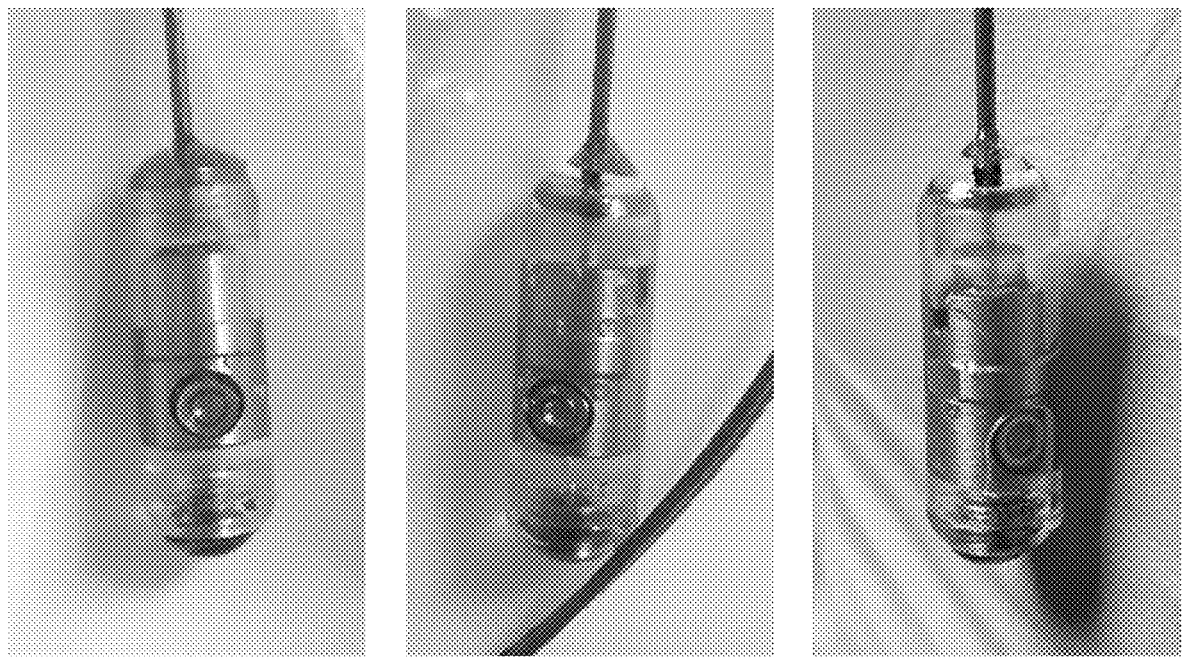
FIG. 2 shows water-filled SECM capsules 1 day (left), 1 week (center), and 1 month (right) after the capsule has been filled with water, showing the progressive effects of water on the probe over time.

The following detailed description includes references to the accompanying drawings, which form a part of the detailed description. The drawings show, by way of illustration, specific embodiments in which the apparatus may be practiced. These embodiments, which are also referred to herein as "examples" or "options," are described in enough detail to enable those skilled in the art to practice the present embodiments. The embodiments may be combined, other embodiments may be utilized or structural or logical changes may be made without departing from the scope of the invention. The following detailed description is, therefore, not to be taken in a limiting sense and the scope of the invention is defined by the appended claims and their legal equivalents. In this document, the terms "a" or "an" are used to include one or more than one, and the term "or" is used to refer to a nonexclusive "or" unless otherwise indicated. In addition, it is to be understood that the phraseology or terminology employed herein, and not otherwise defined, is for the purpose of description only and not of limitation.

DETAILED DESCRIPTION OF THE PRESENT DISCLOSURE

Disclosed herein are embodiments of an apparatus, method, and/or system for an SECM probe which includes an objective lens having a biconic surface and which as a consequence does not require water immersion or other corrective measures to be taken to achieve diffraction-limited or near diffraction-limited optical resolution.

Spectrally encoded confocal microscopy (SECM) is a miniature endomicroscopy technique that encodes physical locations on a specimen using wavelength to achieve fast imaging speeds. Briefly, a broadband or wavelength-swept light source is dispersed across a swath of a sample so that each wavelength or subgroups of wavelengths acts as a separate beam to illuminate a sample (FIG. 3), increasing the amount of data that can be collected from a sample in a single pass since this permits large amounts of data to be collected in parallel. While some pill-sized tethered SECM capsules have been developed to acquire cellular-level resolution images of the upper gastrointestinal (GI) tract, the imaging quality of such SECM capsules to date has been limited by issues including insufficient optical resolution, non-uniform pullback, and non-uniform rotational distortion.

Some versions of water-filled, pill-sized tethered capsules that have been developed have been compatible with 100 kHz, 1310 nm wavelength-swept source SECM imaging systems. Disclosed herein are embodiments of a tethered SECM endomicroscopic imaging system and capsule that utilizes a 400 kHz swept source centered at 1060 nm. In addition to providing higher resolution owing to the shorter wavelength, the new 1060 nm capsule design does not require corrective measures such as water immersion, i.e. filling of the capsule with a liquid such as water.

The need for water immersion or other corrective measures has been eliminated in various disclosed embodiments by designing an objective lens 310 (FIGS. 3, 5) that may have a conventional aspheric surface 320 on one side (e.g. the side facing the source) and a biconic surface 330 on the opposite side (e.g. the side facing the sample) of the objective lens 310 to correct the non-symmetric spherical aberration induced by a curved (generally cylindrical) transparent wall of the capsule.

In various embodiments, a diameter of the capsule has also been increased to improve physical contact with the esophagus and to elongate the spectrally-encoded line length that may be used, resulting in a greater number of wavelengths that may be distinguished and hence a greater number of pixels in the swath of spectrally-spread light. In various embodiments, compared to other SECM capsule devices and systems using a 100 kHz, 1310 nm source, the imaging speed of the presently-disclosed design may be increased by a factor of 5.2, and the lateral resolution may be improved by 15%. Furthermore, the implementation of SECM without water immersion of the capsule simplifies the manufacturability and increases the lifetime of the devices. These advances significantly enhance the clinical translatability of SECM for applications such as upper gastrointestinal tract diagnosis.

Figure 3:
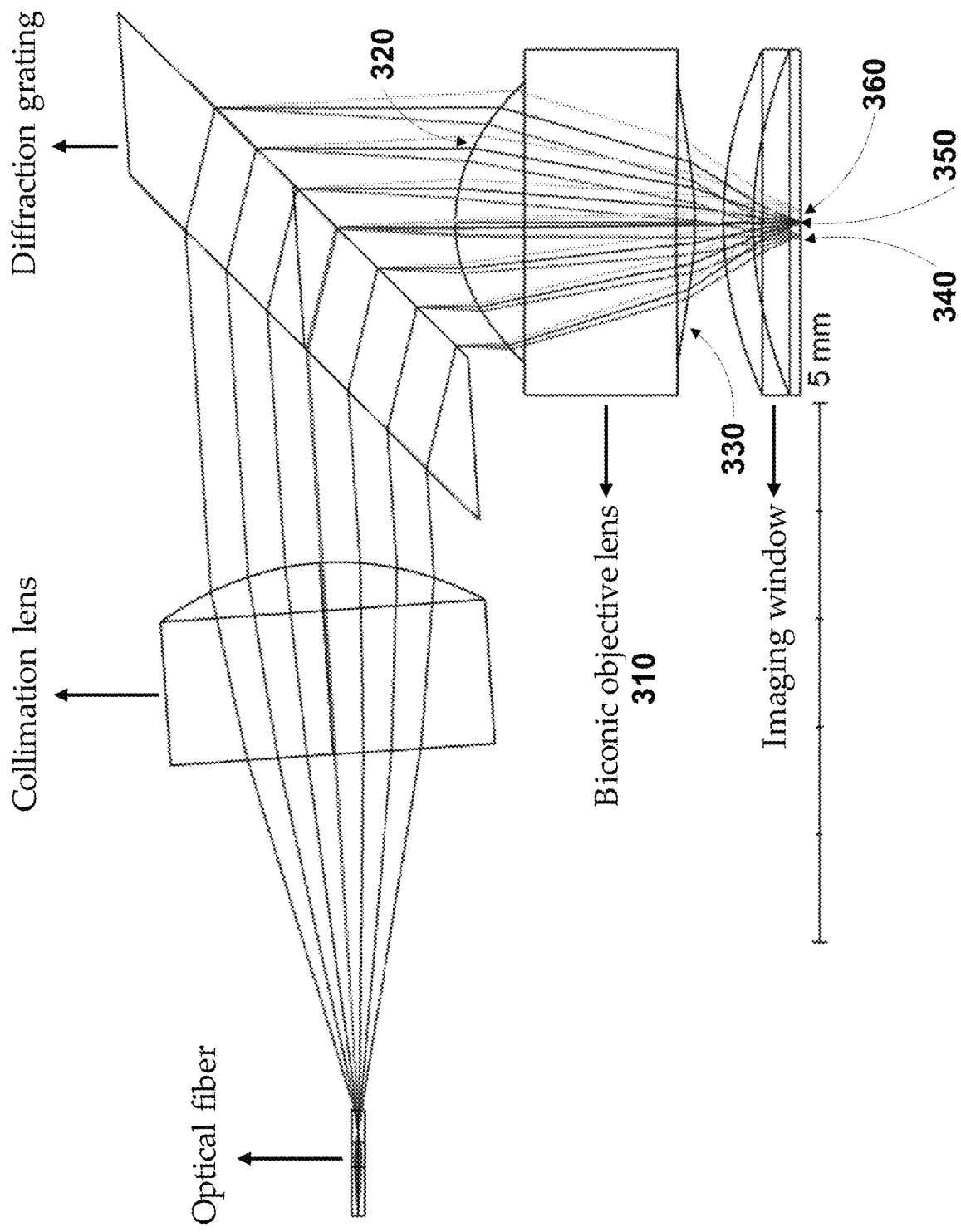
FIG. 3 shows an SECM optical arrangement for use in a capsule and which includes an objective lens having a biconic surface facing the imaging window.
Figure 4:
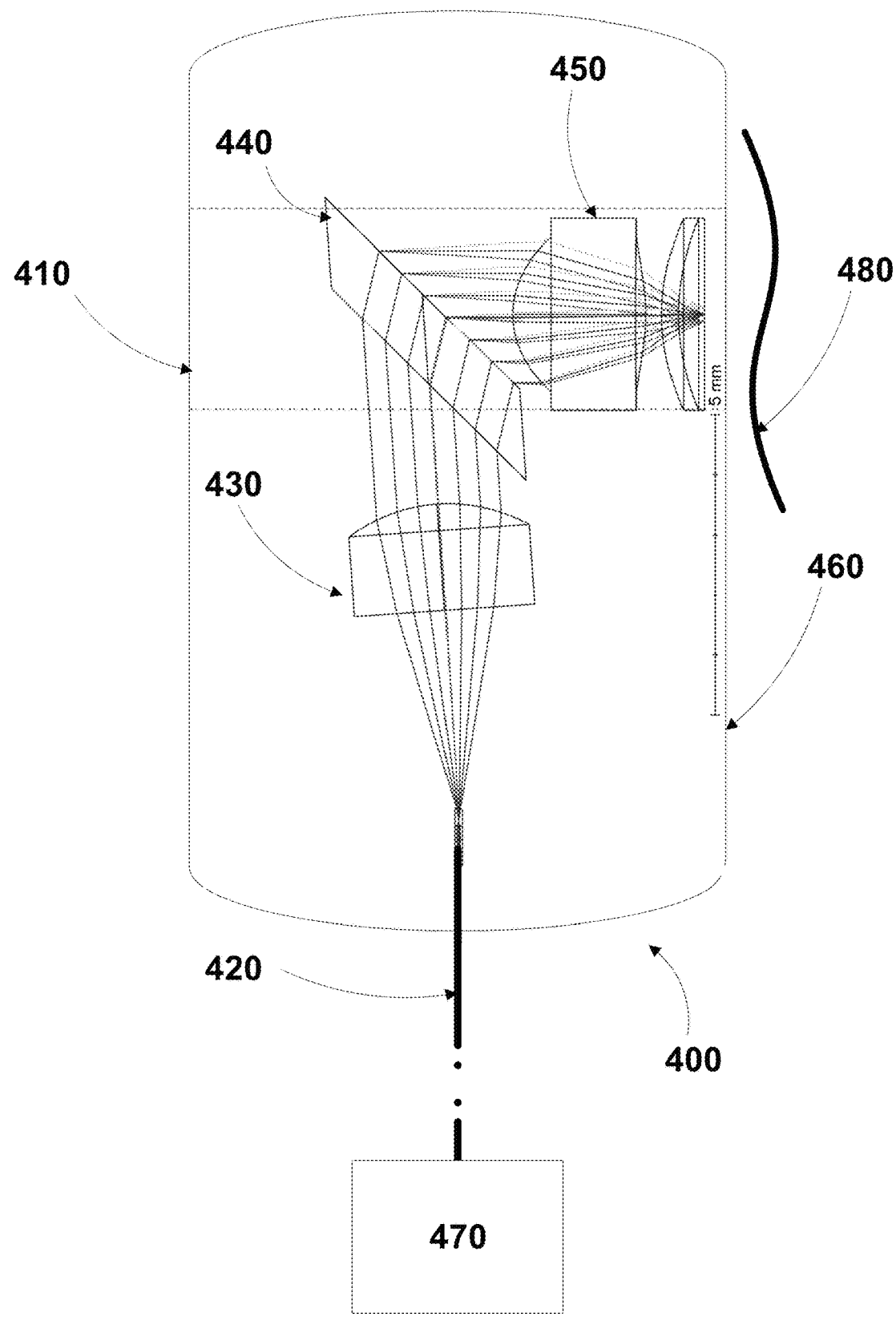
FIG. 4 shows a tethered capsule with SECM optics disposed therein.

In general, SECM permits reflectance confocal microscopy to be performed through a compact probe, such as a catheter or capsule (FIG. 4). SECM uses wavelength division multiplexing ("WDM") to encode one-dimensional spatial information reflected from the sample. The fast scanning axis is replaced by a series of focused points with each location being represented by a different wavelength of light 340, 350, 360 (FIG. 3). The remittance as a function of spatial position can be determined by measuring the spectrum of the reflected light. A two-dimensional image may be created by scanning the wavelength-encoded axis by slow mechanical motion of the probe. Thus, endoscopic devices embodying the invention allow SECM imaging of a variety of tissues and organs either integrated with standard endoscopes or as stand-alone devices such as capsules. See U.S. Pat. No. 6,831,781, and US Pat. Appl. Publ. 2011/013178, each of which is incorporated by reference herein in its entirety for all purposes.

In some embodiments, an SECM system can be constructed in a swallowable, tethered capsule 400 (FIG. 4). As shown in FIG. 4, the capsule 400 includes an imaging window 410 (indicated with dashed lines), a tether 420 which includes a waveguide/optical fiber, a collimating lens 430, a diffraction grating 440, an objective lens 450, and a housing 460. The tether 420 connects to an SECM system 470 which in various embodiments may include one or more of a light source (e.g. a swept-source laser), a rotational and/or linear scanning system, a light detector, and a computing system for controlling one or more other components and for collecting and processing data.

In various embodiments, the overall shape of the capsule 400 may be smooth, with the housing 460 including a cylindrical body having rounded (e.g. hemispherical) ends. This overall shape permits the capsule 400 to be swallowed and to move through luminal passages such as the GI tract with low resistance to permit it to move by gravity and/or peristaltic muscular movements, where the tether 420 extends from one end of the housing 460 (FIG. 4). The size of the capsule 400 may vary but in general is less than 10 mm in diameter and in some embodiments is 7 mm and in other embodiments is 8 mm. At least a portion of the housing 460 of the capsule 400 includes an imaging window 410 which is optically transparent to suitable wavelengths (e.g. at UV, visible, and/or IR wavelengths); in general the imaging window 410 extends completely around the perimeter of the capsule 400 to permit rotational scanning of the sample through the capsule housing 460.

Light from a waveguide housed within the tether 460 is directed towards the diffraction grating 440 which is set at an angle relative to the waveguide (e.g. an approximately 45° angle) and light exiting the diffraction grating 440 is directed to the objective lens 450 which in turn focuses the light through the side of the capsule 400 and towards a tissue 480 (FIG. 4). The objective lens 450 (described further below) in some embodiments may have a first side facing the diffraction grating 440 that has an aspheric surface and a second side facing towards the outside of the capsule 400 and the tissue 480 that has a biconic surface. As described further below, the biconic surface is designed to correct for aberrations that may be caused by the curved/cylindrical outer surface of the capsule body (i.e. the imaging window 410) through which imaging occurs. In some embodiments a collimating lens 430 may be placed between the output of the waveguide and the diffraction grating 440. Given that the optical components inside the probe are rotatable, there is a gap between the objective lens 450 and the imaging window 410 to facilitate free rotation of the optical components within the capsule 400. In certain known devices this gap has been filled with water, food-grade oil, mineral oil, or other medical- or food-grade liquids (generally liquids having similar viscosity to water which are optically transparent) to reduce aberrations from the curved imaging window 410, however the biconic surface of the objective lens 450 disclosed herein corrects for these aberrations without the need for a liquid such as water to fill the gap. Instead of filling the space within the housing 460 with a liquid such as water, the space may be filled with a gas such as air, nitrogen, or any other suitable (e.g. medically-approved) gas.

As discussed further below, a spectral source (e.g. a swept source laser) may be used for an SECM implementation. Light from the source that is emitted through the side of the capsule and onto the tissue is distributed in a linear arrangement extending in a direction parallel to the long axis of the capsule, where the different wavelengths of the spectral source are distributed along a line. Light reflected from the sample is then transmitted through the capsule and the waveguide to the SECM system 470 for constructing into images.

For luminal samples such as portions of the GI tract (e.g. the esophagus or other regions) the capsule may collect image data while it is moving downward through the luminal structure (e.g. during swallowing) or in the reverse direction during retrieval of the capsule. The optical components may rotate in order to obtain image data from the full circumference of the luminal sample while the capsule is translated (e.g. pulled up) through the luminal sample, which produces a spiral scan of the sample that can be presented using polar or rectangular coordinates.

Figure 5:
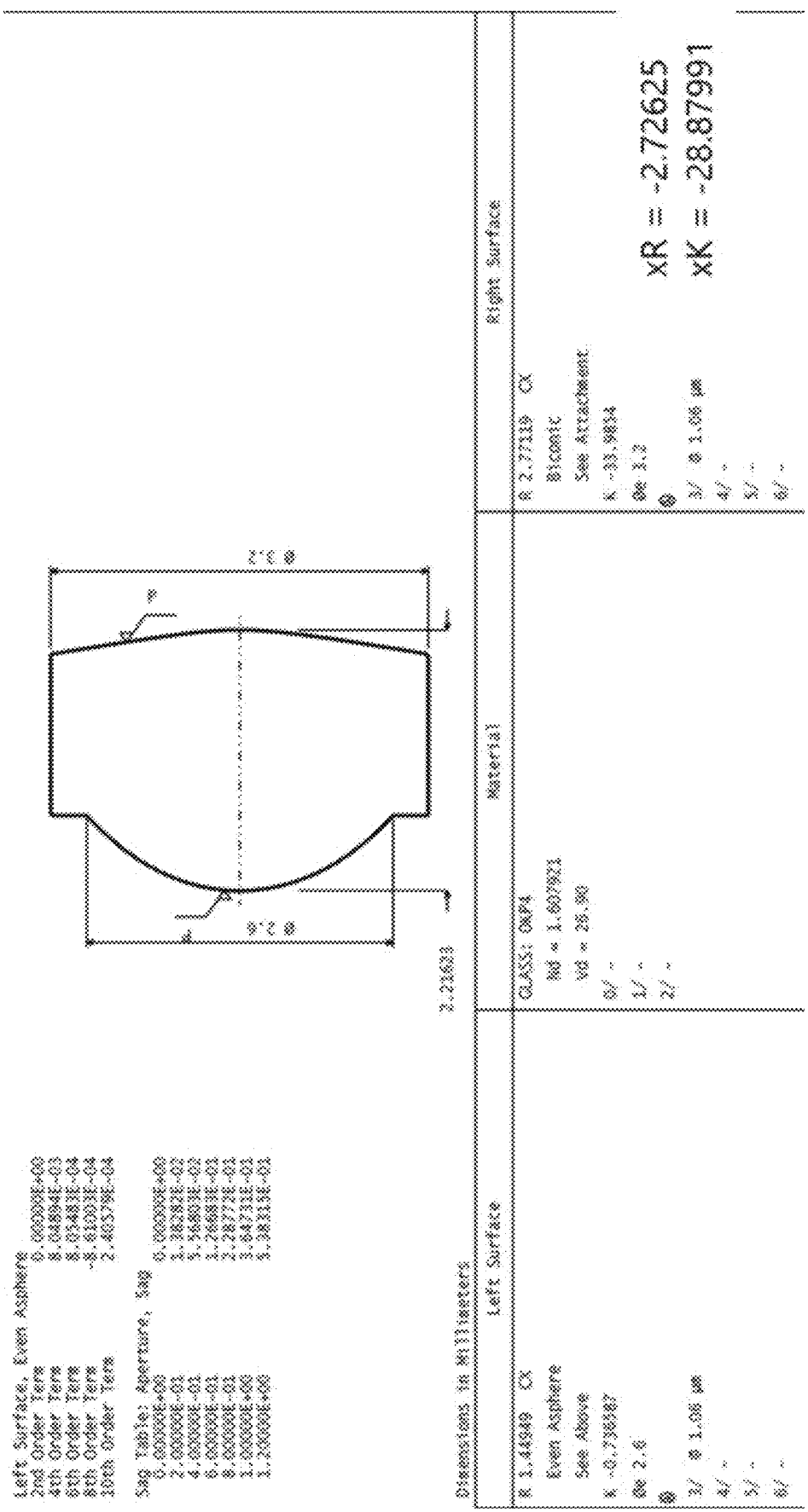
FIG. 5 shows a diagram of a lens generated using ZEMAX software which includes lists of parameters for a particular embodiment of the aspheric surface, the biconic surface, and the lens material.

In various embodiments, the lens includes an aspheric surface and a biconic surface. The lens may be machined or injection molded from glass or plastic. The lens may be machined through diamond turning using a polymer such as OKP4 or PMMA or fabricated via injection molding using glass materials such as D-ZK3. In some embodiments, injection molding of the lens is expected to reduce the cost per unit significantly, e.g. to as low as $10 per unit. In other embodiments the aspheric lens may have a radius of approximately 1.45 mm, although larger or smaller radii are also possible. In certain embodiments the index of refraction may be between 1.5 and 1.7 and in one particular embodiment is 1.607 for OKP4 plastic. FIG. 5 shows a diagram of a lens generated using ZEMAX software which includes lists of parameters for a particular embodiment of the aspheric surface, the biconic surface, and the lens material.

Although the outer circumference of a lens having a biconic surface may be circular, the biconic surface of the lens includes a raised portion that is not radially symmetric. Instead, the raised portion has two axes, e.g. an x-axis and a y-axis, each of which has an associated radius of curvature and conic constant, K. One of the axes has a larger radius of curvature and conic constant compared to the other axis, so that the lens is oriented within the capsule with the axis having the larger radius of curvature and conic constant being parallel to the axis of the cylindrical imaging window and the long axis of the cylindrical housing (see FIG. 10). The overall shape of the biconic lens, defined at least in part by the radii and conic contants of the x- and y-axes, is selected so that it corrects for aberrations caused by the capsule housing, in particular the transparent curved imaging window, and in general the lens characteristics are matched for use with a particular imaging window. In some embodiments the radius of the x-axis is −2.676 and the conic constant of the x-axis is −27.735, and the radius of the y-axis is −2.725 and the conic constant of the y-axis is −32.572, although biconic lenses with other radii and conic constants may be used.

Figure 6:
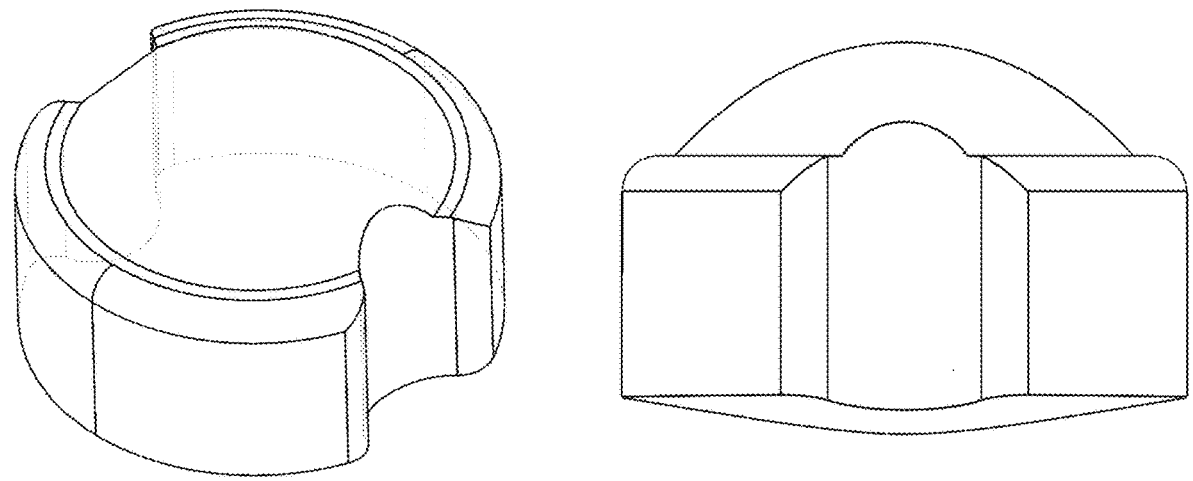
FIG. 6 shows a design of an objective lens having an aspheric surface and a biconic surface which includes a notch for correctly aligning the lens, where the lens is shown in perspective (left) and from the side (right).
Figure 7:
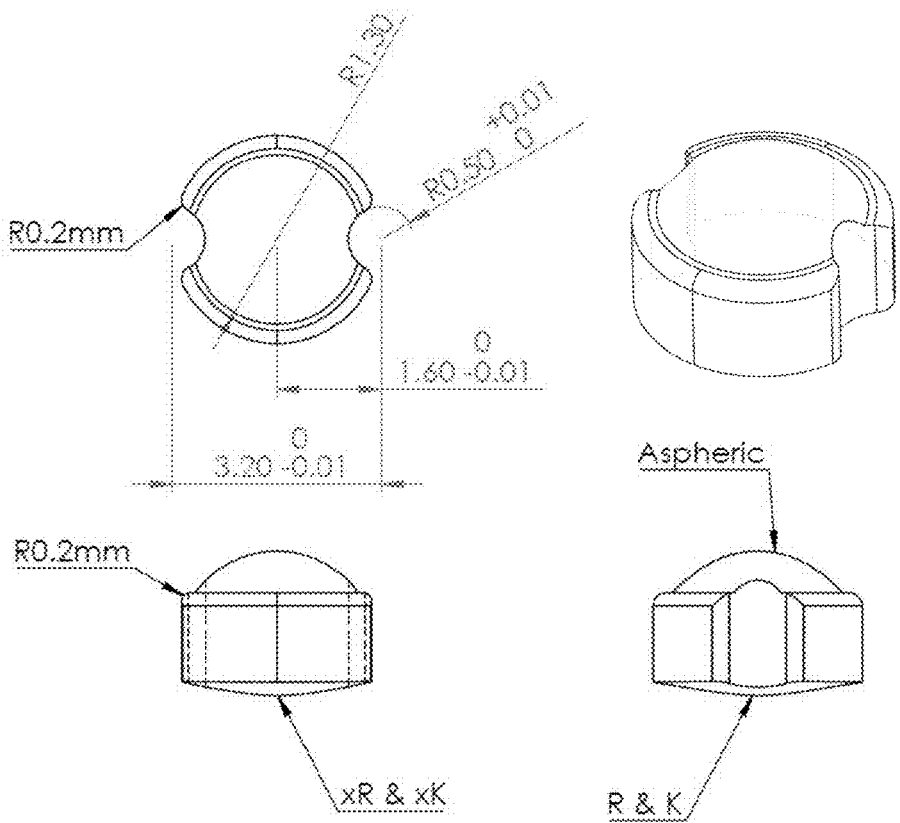
FIG. 7 shows another design of an objective lens having an aspheric surface and a biconic surface which includes two notches for correctly aligning the lens, where the lens is shown from an end (top left), in perspective (top right), from a first side (lower left), and from a second side orthogonal to the first side (lower right).
Figure 8:
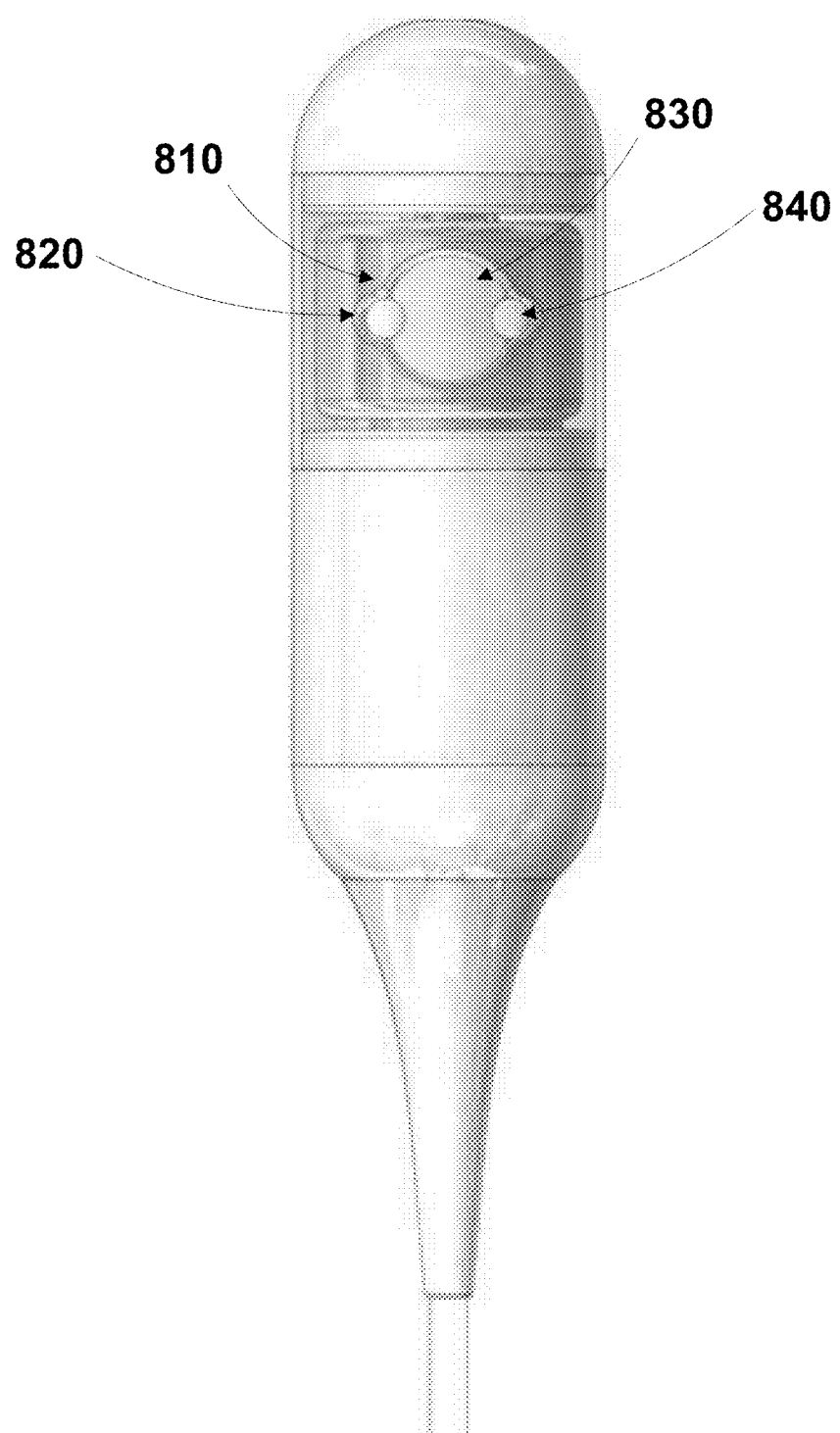
FIG. 8 shows a tethered capsule which includes an objective lens mount having a pair of rounded notches and a lens with a similar pair of rounded notches in which two ceramic spheres are inserted into the spaces created by the notches to secure the lens in place in the correct orientation.

Given that the biconic surface of the lens has an elongated, non-radially symmetric shape, in some embodiments the lens may include one or more features such as markings or notches to ensure proper alignment of the lens relative to the other optical components and the capsule housing. For example, the lens may include one (FIG. 6) or two (FIG. 7) notches on the outer edge to facilitate alignment of the lens, although other shapes and numbers of alignment features are possible. The notched lens fits into a receptacle having a complementary shape which secures the lens in the correct orientation (FIG. 8). In the embodiment shown in FIG. 8, an objective lens mount 810 includes rounded notches 820 such as those shown in the lens in FIG. 7 and the lens 830 is secured in place using two spherical or cylindrical inserts, for example ceramic spheres 840. Nevertheless, other shapes and styles of notches and inserts may be used and in some embodiments the lens or the receptacle may include one or more protrusion that is complementary to a notch or other shape in the receptacle or lens, respectively.

The light source for SECM may be either a broad bandwidth or a wavelength-swept source. Relative to previous embodiments of SECM (particularly capsule-based SECM) which used swept sources with a center wavelength of 1310 nm and repetition rates of 100 kHz, utilizing a swept-source laser with shorter wavelength and higher repetition rate as disclosed herein improves both optical resolution and imaging speed. In various embodiments, the capsule-based system disclosed herein provides techniques that utilize a swept-source laser with the wavelength centered at shorter wavelengths such as 1060 nm, ranging from 1020 nm-1100 nm, and with faster repetition rates such as 400 kHz. In one particular embodiment the source is Model AXP50124-3 from Axsun Technologies, Billerica, MA Given that optical resolution is a function of wavelength, with shorter wavelengths providing smaller diffraction-limited focal spot sizes and therefore better resolution than longer wavelengths, the shorter-wavelength sources disclosed herein provide higher optical resolution compared to previously-used 1300 nm range lasers. Furthermore, the 400 kHz repetition rate of the disclosed laser significantly reduces motion artifacts that were observed in previous 100 kHz laser systems.

The table in FIG. 9 presents a comparison of specifications for the present system (right, "SECM-TCE-1060") and a prior system (left, "SECM-TCE-1310") of optics for a capsule-based SECM system. As noted in FIG. 9, the presently-disclosed embodiments do not require immersion of the optics in a liquid such as water, which as discussed above simplifies the manufacture and lengthens the useful lifetime of the devices. In addition, the central wavelength is significantly shorter (1060 nm vs. 1290 nm), which provides improved resolution. The capsule diameter in certain embodiments is increased from 7 mm to 8 mm, which increases physical contact between the capsule and surrounding tissue such as the esophagus and also provides an elongated spectrally-encoded line length, which in turn increases the number of pixels/samples that can be distinguished. The imaging field of view is increased from 260 μm to 340 μm and the lateral resolution is improved from 1.44

μm to 1.25 μm while the imaging depth improves from 50 μm to 100 μm. Finally, devices using a lens with a biconic surface are operated with a 90° imaging angle, compared to the 95.725° imaging angle used in the previous device. Having an imaging angle that is approximately perpendicular to the imaging window improves image quality because the biconic surface of the objective lens is in the best orientation to correct for the aberrations arising from the curved surface of the curved imaging window.

Figure 10:
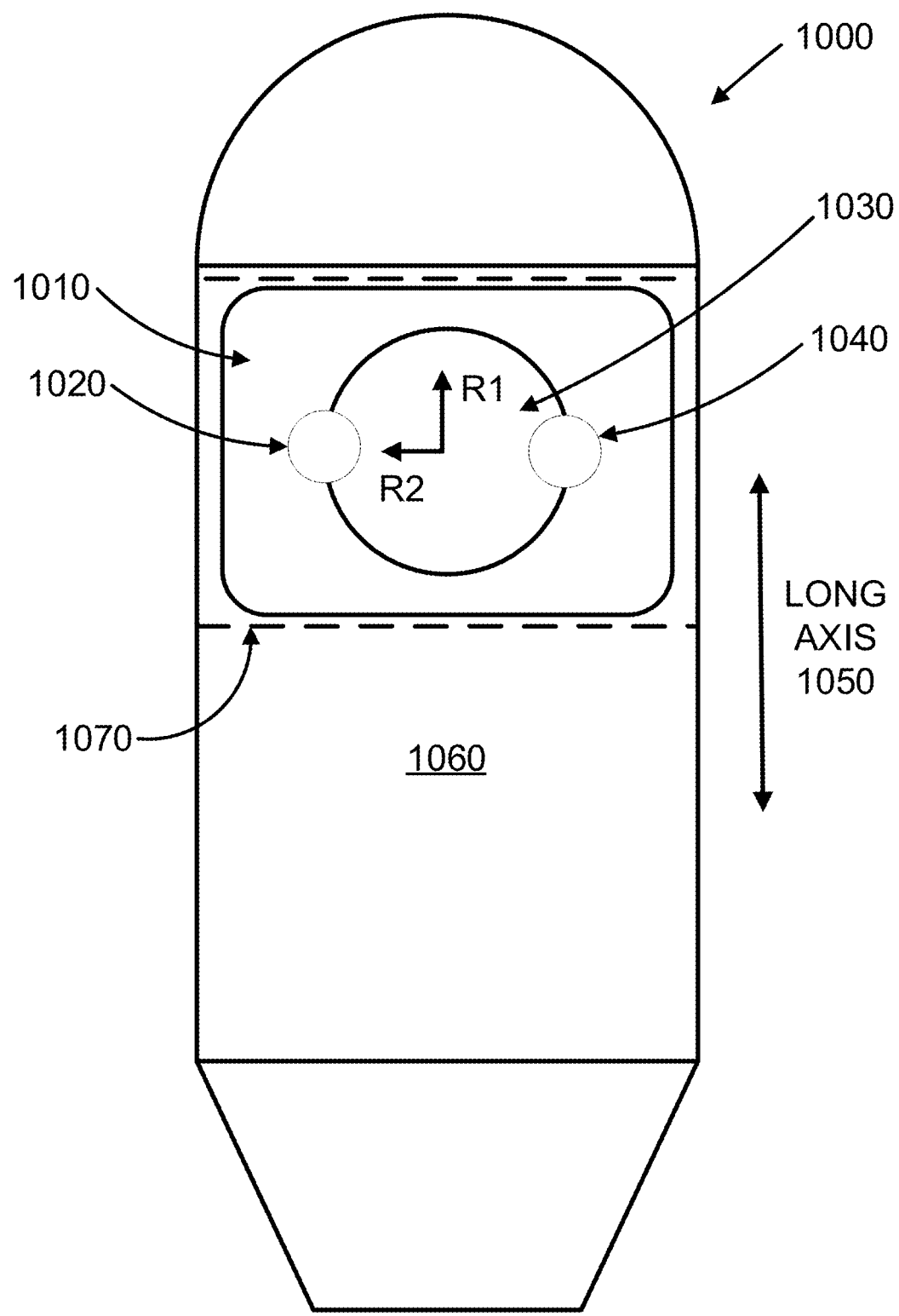
FIG. 10 shows a diagram of a capsule probe with a cylindrical housing in which the long axis of the probe is indicated along with the radii of the biconic lens of the optical components within the probe, where a first axis (R1) is parallel to the long axis of the probe and perpendicular to a second, shorter axis (R2).

FIG. 10 shows a diagram of an embodiment of a capsule probe 1000 including a cylindrical housing 1060 in which the long axis 1050 of the probe is indicated along with the radii of the biconic lens of the optical components within the probe, where a first axis R1 (associated with a first radius of curvature and a first conical constant) is parallel to the long axis 1050 of cylindrical housing 1060 of the probe 1000 and perpendicular to a second axis R2 (associated with a second radius of curvature and a second conical constant), where the first radius of curvature and first conical constant are greater than the second radius of curvature and second conical constant. A window 1070, which in certain embodiments is a transparent cylindrical surface, is shown with dashed lines, where the window 1070 is included within the cylindrical housing 1060. Also indicated are an objective lens mount 1010 which includes rounded notches 1020 in which lens 1030 may be secured in place using two spherical or cylindrical inserts 1040, for example ceramic spheres, to maintain the lens 1030 in the correct orientation with the first axis R1 being parallel to the long axis 1050 of the cylindrical housing 1060.

Although the examples disclosed herein are generally shown in the context of capsule-based SECM, the disclosed apparatus and methods are more generally applicable for use with any probe that is subject to aberrations from a curved (e.g. cylindrical) imaging window. Thus, the disclosed objective lens having a biconic surface can be used in probes such as capsules to implement various imaging modalities including but not limited to OCT, OFDI, SD-OCT, and other scanning imaging modalities.

It will be appreciated by those skilled in the art that while the disclosed subject matter has been described above in connection with particular embodiments and examples, the invention is not necessarily so limited, and that numerous other embodiments, examples, uses, modifications and departures from the embodiments, examples and uses are intended to be encompassed by the claims attached hereto. The entire disclosure of each patent and publication cited herein is hereby incorporated by reference, as if each such patent or publication were individually incorporated by reference herein.

Various features and advantages of the invention are set forth in the following claims.

What is claimed is:

1. A probe for performing endomicroscopy, comprising:
a light source;
a waveguide coupled to the light source;
a diffraction grating,
the waveguide directing light from the light source to the diffraction grating; and
a lens having a first aspheric surface and a second biconic surface,
the second biconic surface having a first axis associated with a first radius of curvature and a second axis associated with a second radius of curvature,
the second axis being perpendicular to the first axis, the first radius of curvature and the second radius of curvature having the same sign, and
diffracted light from the diffraction grating being directed into the aspheric surface of the lens and being emitted from the biconic surface of the lens towards a transparent cylindrical surface of the probe.

2. The probe of claim 1, wherein the lens is contained within a housing, and
wherein the housing comprises the transparent cylindrical surface.

3. The probe of claim 2, wherein the housing does not contain a liquid.

4. The probe of claim 2, wherein the lens is immersed in a gas within the housing.

5. The probe of claim 4, wherein the gas comprises air.

6. The probe of claim 2, wherein
the first radius of curvature is larger than the second radius of curvature.

7. The probe of claim 6, wherein the lens is configured so that the first axis is oriented parallel to a long axis of the transparent cylindrical surface of the probe.

8. The probe of claim 7, wherein the first axis is associated with a first conical constant and the second axis is associated with a second conical constant, and
wherein the first conical constant is larger than the second conical constant.

9. The probe of claim 1, further comprising a collimation lens disposed between the waveguide and the diffraction grating,
wherein the light from the waveguide passes through the collimation lens to the diffraction grating.

10. The probe of claim 1, wherein the probe comprises a tethered capsule.

11. The probe of claim 10, wherein the tethered capsule has an outside diameter of 8 mm.

12. The probe of claim 1, wherein the biconic surface of the lens is shaped to correct for spherical aberrations from the transparent cylindrical surface of the probe.

13. The probe of claim 1, wherein the source comprises a swept source laser.

14. The probe of claim 13, wherein the swept source laser has a center wavelength of 1060 nm and a repetition rate of 400 kHz.

15. The probe of claim 14, wherein a target imaging depth of the probe is 100 μm and wherein a lateral resolution of the probe is 1.25 μm.

16. The probe of claim 13, wherein the endomicroscopy comprises spectrally-encoded confocal microscopy (SECM).

17. The probe of claim 1, wherein the lens comprises a notch for alignment of the lens.

18. A method for performing endomicroscopy, the method comprising:
providing a probe comprising a light source, a waveguide coupled to the light source, a diffraction grating, and a lens having a first aspheric surface and a second biconic surface,
the second biconic surface having a first axis associated with a first radius of curvature and a second axis associated with a second radius of curvature,
the second axis being perpendicular to the first axis, and
the first radius of curvature and the second radius of curvature having the same sign,
directing light from the light source to the diffraction grating, and
directing diffracted light from the diffraction grating into the aspheric surface of the lens and being emitted from the biconic surface of the lens towards a transparent cylindrical surface of the probe.

19. The method of claim 18, wherein the lens is contained within a housing, and wherein the housing comprises the transparent cylindrical surface.

20. The method of claim 19, wherein the housing does not contain a liquid.

21. The method of claim 19, wherein the lens is immersed in a gas within the housing.

22. The method of claim 21, wherein the gas comprises air.

23. The method of claim 19, wherein
the first radius of curvature is larger than the second radius of curvature.

24. The method of claim 23, wherein the lens is configured so that the first axis is oriented parallel to a long axis of the transparent cylindrical surface of the probe.

25. The method of claim 24, wherein the first axis is associated with a first conical constant and the second axis is associated with a second conical constant, and
wherein the first conical constant is larger than the second conical constant.

26. The method of claim 18, wherein directing light from the light source to the diffraction grating further comprises:
directing light from the light source from the waveguide to a collimation lens disposed between the waveguide and the diffraction grating,
wherein the light from the collimation lens is directed to the diffraction grating.

27. The method of claim 18, wherein the probe comprises a tethered capsule.

28. The method of claim 27, wherein the tethered capsule has an outside diameter of 8 mm.

29. The method of claim 18, wherein the biconic surface of the lens is shaped to correct for spherical aberrations from the transparent cylindrical surface of the probe.

30. The method of claim 18, wherein the source comprises a swept source laser.

31. The method of claim 30, wherein the swept source laser has a center wavelength of 1060 nm and a repetition rate of 400 kHz.

32. The method of claim 31, wherein a target imaging depth of the probe is 100 µm and wherein a lateral resolution of the probe is 1.25 µm.

33. The method of claim 30, wherein the endomicroscopy comprises spectrally-encoded confocal microscopy (SECM) and wherein the probe is an SECM probe.

34. The method of claim 18, wherein the lens comprises a notch for alignment of the lens.

* * * * *